United States Patent [19]
Kang et al.

[11] Patent Number: 5,582,882
[45] Date of Patent: Dec. 10, 1996

[54] FLUORINE CONTAINING ORGANO-POLYMERIC MATERIAL FOR ALIGNMENT LAYER AND LIQUID CRYSTAL DISPLAY DEVICE EMPLOYING THE SAME

[75] Inventors: Shin-woong Kang, Seoul; Sung-ho Jin, Suwon, both of Rep. of Korea

[73] Assignee: Samsung Display Devices Co., Ltd., Kyungki-do, Rep. of Korea

[21] Appl. No.: 461,701

[22] Filed: Jun. 5, 1995

[30] Foreign Application Priority Data

Jan. 27, 1995 [KR] Rep. of Korea ............... 95-1584

[51] Int. Cl.$^6$ ................... G02F 1/1337
[52] U.S. Cl. ................... 428/1; 349/123

[58] Field of Search ................ 428/1; 359/75–79

[56] References Cited

U.S. PATENT DOCUMENTS 5,239,398  8/1993  Yanagisawa et al. ............ 428/1

*Primary Examiner*—Alexander Thomas
*Attorney, Agent, or Firm*—Morgan & Finnegan LLP

[57] ABSTRACT

Disclosed are a sulfonium precursor polymer of fluorine-containing poly-1,4-phenylenevinylene precursor polymer used as an aligning material of a liquid crystal device, and a liquid crystal device comprising fluorine-containing poly-1,4-phenylenevinylene as an alignment layer. Uniform orientation and a large pretilt angle can be accomplished.

3 Claims, 1 Drawing Sheet

FLUORINE CONTAINING ORGANO-POLYMERIC MATERIAL FOR ALIGNMENT LAYER AND LIQUID CRYSTAL DISPLAY DEVICE EMPLOYING THE SAME

BACKGROUND OF THE INVENTION

The present invention relates to an organo polymeric material for liquid crystal orientation having a characteristic of increasing a pretilt angle and a liquid crystal display device employing the same as an alignment layer.

Generally, liquid crystal has both the fluidity of liquid and the optical properties of crystal and so is classified as a material having a mesophase between liquid and solid. Optical properties of the liquid crystal can be changed by either an electric field or heat. Liquid crystal display (LCD) devices using these properties of liquid crystal are one of the representative of flat panel display devices, along with plasma display and light emitting diode. FIG. 1 illustrates a cross-sectional view of a general LCD. In FIG. 1, reference numerals 1 and 1' represent polarizing plates, reference numerals 2 and 2' represent substrates, reference numerals 3 and 3' represent electrodes, reference numerals 4 and 4' represent insulating films, reference numerals 5 and 5' represent orientation layers, a reference numeral 6 represents a spacer and a reference numeral 7 represents a liquid crystal layer.

Physical properties of the liquid crystal are liable to change according to the molecular arrangement and so response characteristics thereof are greatly changed according to an external force such as an electric field. Also, since the pretilt angle of the liquid crystal is changed according to the material of the alignment layer and/or orientation treatment method, the concept of control of the pretilt angle of the liquid crystal could be understood by the control of the orientation of the liquid crystal molecules. FIG. 2 illustrates an azimuth relation of the liquid crystal molecules and the orientation surface, that is, the substrate. Here, the pretilt angle (θ) is an angle made by a substrate and a director of the liquid crystal, and azimuth angle of a liquid crystal director is represented as ψ.

Uniform alignment of the liquid crystal is not easily obtained by simply injecting the liquid crystal between upper and lower substrates. Therefore, generally, an orientation layer is formed on the substrate to obtain uniform orientation of the liquid crystal.

Alignment material which can control the pretilt angle of the liquid crystal as described above is essential in enhancing display characteristics of the LCD. In the case of a super twisted nematic LCD (STN-LCD), a large pretilt angle of the liquid crystal is needed to prevent the generation of a defect line, and while in the case of a thin film transistor LCD (TFT-LCD), orientating materials having a small pretilt angle and a large pretilt angle are used as an upper substrate or a lower substrate, respectively (and vice versa) to enhance the viewing angle (Journal of the SID 2/2, 31, 1994). For the case of a surface stabilized FLCD (SSFLCD) which is liable to generate orientation defects and has poor mechanical shock resestance, alignment materials having a large pretilt angle are used to change the structure of the smectic layer to compensate for the defects (Japan Display '92, 53 & 523). However, most of the commercially available conventional alignment materials have a small pretilt angle and the change of the pretilt angles thereof is greatly changed according to the change of conditions such as baking temperature and orientation condition during manufacture of the device.

Polyimide resin film has been widely used as an alignment material to orientate the liquid crystal molecules. The liquid crystal molecules are arranged along a rubbing direction and are orientated with a pretilt angle of 1°–3° by means of rubbed polyimide film formed on a substrate with a cloth in a predetermined direction. However, through this method of using rubbed organic resin film formed on the substrate, the pretilt angle of the liquid crystal molecules may only slightly be increased.

Another method of obtaining a large pretilt angle is an obliqud evaporation method of inorganic material such as silicon oxide without rubbing. However, the obliqud evaporation of inorganic material is complex and is not appropriate in practical production on an industrial scale, when compared with the rubbing method using organic resin film.

To solve these problems, the present inventors synthesized organic polymer containing fluorine, applied the material as an alignment material for an LCD and discovered after repeated research and development, that both uniform orientation and a large pretilt angle of the liquid crystal molecules can be obtained.

SUMMARY OF THE INVENTION

An object of the present invention is to provide a sulfonium precursor polymer as a precursor of fluorine-containing poly-1,4-phenylenevinylene (F-PPV) which can be used as an alignment material for a liquid crystal.

Another object of the present invention is to provide an LCD where fluorine-containing poly-1,4-phenylenevinylene (F-PPV) converted from the sulfonium precursor polymer thereof during the manufacture of the LCD is employed as an alignment material, so that the pretilt angle of the liquid crystal is properly controlled, thereby enhancing display characteristics of the LCD.

To accomplish the object of the present invention, there is provided a sulfonium precursor polymer represented as the following formula of (I), which is converted to fluorine-containing poly-1,4-phenylenevinylene by heat treatment when employed as an alignment layer of a liquid crystal display device.

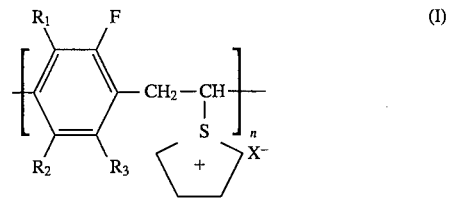

(I)

Here, $R_1$, $R_2$ and $R_3$ are independently H or F, X is Br or Cl, and n is an integer of 100 or more.

The other object of the present invention is accomplished by a liquid crystal device comprising a pair of upper and lower substrates, transparent electrodes formed on each substrate, alignment layers formed on each transparent electrode and liquid crystal injected between said alignment layers, characterized in that said orientation layer comprises fluorine-containing poly-1,4-phenylenevinylene represented as the following formula (II).

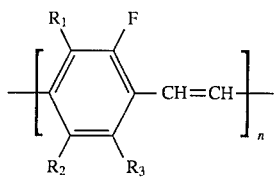

$$\left[ \begin{array}{c} R_1 \\ \\ R_2 \end{array} \begin{array}{c} F \\ \\ R_3 \end{array} - CH=CH \right]_n \quad (II)$$

Here, $R_1$, $R_2$ and $R_3$ are independently H or F, and n is an integer of 100 or more.

The range of pretilt angle of the liquid crystal of the LCD according to the present invention is larger than the conventional one and is 5° to 20°.

BRIEF DESCRIPTION OF THE DRAWINGS

The above objects and advantages of the present invention will become more apparent by describing in detail a preferred embodiment thereof with reference to the attached drawings in which.

DETAILED DESCRIPTION OF THE INVENTION

Figure 1:
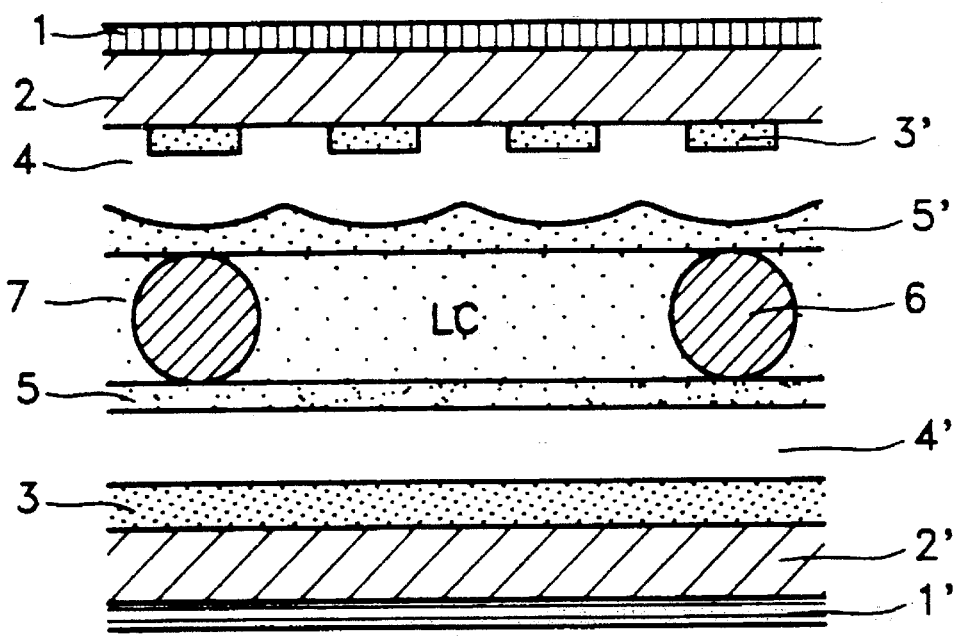
FIG. 1 illustrates a cross-sectional view of a general LCD.
Figure 2:
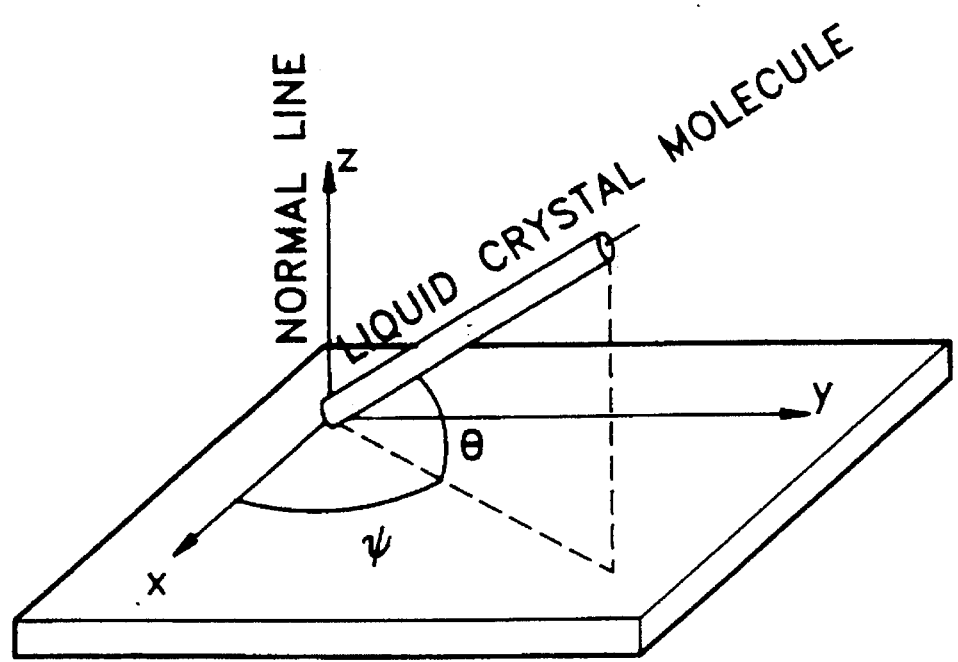
FIG. 2 illustrates an azimuth relation of the liquid crystal molecules and the orientation surface (substrate).

F-PPV of the alignment layer of the LCD according to the present invention is an organic polymer where PPV having polyconjugated double bonds has fluorine substituents, and is formed by conversion of a precursor polymer having a good processability by heat treatment.

The precursor polymer is dissolved in solvents such as methanol, water, etc. A precursor polymer solution of an appropriate concentration is coated on a transparent electrode formed on the substrate and is heated to 200°–400° C. to remove sulfonium moiety and to form a polymer film having polyconjugated double bonds in a thickness of 0.01–1 μm. That is, to obtain uniform orientation characteristics by controlling the pretilt angle of the liquid crystal in the present invention, a liquid crystal orientation layer is manufactured by coating fluorine-containing PPV precursor polymer (that is, sulfonium precursor polymer) on the transparent electrode formed on the substrate, heating the precursor polymer to form the orientation layer and then rubbing the orientation layer. The thus formed F-PPV organo polymeric film is uniform without any pinholes or other defects, is stable to oxygen and moisture in the air or chemicals and has heat-resistance even at high temperature of 350° C. or above. Further, it has a good adhesiveness to the substrate.

Hereinbelow, the present invention will be described in detail referring to preferred embodiments. However, the embodiments are only to explain the present invention and should not be understood to restrict the scope of the present invention thereto.

EXAMPLE 1

2-Fluoro-1,4-bis(bromomethyl)benzene was synthesized through a reaction of NBS (N-bromosuccinimide) and 2-fluoro-p-xylene in tetrachloromethane. Tetrahydrothiophene was added in excess and the mixture was reacted in methanol at 45° C. for 20 hours. After completion of the reaction, the mixture was concentrated to a volume of ⅓ and was poured into an excess amount of cold acetone to obtain a monomer of 2-fluoro-1,4-phenylene dimethylene bis(tetrahydrothiophenium)bromide as a white powder. This monomer was dissolved in water and the resultant was cooled to 0° C. Aqueous NaOH solution of the same equivalent amount cooled to 0° C. was added to and reacted with the monomer solution while stirring strongly. After completion of the reaction, the mixture was neutralized using a diluted aqueous acid solution. The thus prepared precursor polymer was injected into a dialysis tube and was dialyzed in methanol for 3 days to obtain a purified precursor polymer.

EXAMPLE 2

The sulfonium precursor polymer of 2-fluoro-poly(1,4-phenylenevinylene) obtained in example 1 was dissolved in methanol and this solution was spin coated on transparent electrodes formed on upper and lower substrates. The coated solution was pre-dried for 5 minutes at 100° C. and baked for 2 hours at 260° C. Both substrates were rubbed unidirectionally with rayon cloth. Sealing agent was printed on one substrate for binding and sealing of the upper and lower substrates. Spacers were dispersed on the other substrate to keep a constant cell distance. The two substrates were attached face to face and constant pressure was applied while heating to cure the sealing agent and to manufacture a void cell. Liquid crystal (ZLI-2293, Merck co.) was injected in the cell and the pretilt angle was measured. The pretilt angle at an environmental temperature was as large as 15°.

COMPARATIVE EXAMPLE

SE-150 (Nissan Chemical Industries Ltd.) was used as an orientating material for comparison. The material was spin coated for 20 seconds, pre-dried at 80° C. for 15 minutes, baked at 260° C. for 60 minutes and rubbed. An LCD was manufactured according to the same process and pretilt angle thereof was measured as described in Example 1. The pretilt angle was about 4°.

As described above, by synthesizing and applying a novel liquid crystal aligning materials in manufacturing the LCD of the present invention, the following effects could be obtained.

First, a higher pretilt angle than those from the commonly used aligning materials could be accomplished.

Second, the LCD had a good orientation stability under the change of conditions during manufacture of the device and so excellent characteristics could be obtained.

Third, since F-PPV of the present invention has a good light transmittance and environmental resistance such as chemical stability, adhesiveness to the substrate, capability to be formed to a uniform thin film and excellent liquid crystal-orientation characteristics by rubbing, display characteristics can be greatly improved when applied to STN-LCD, TFT-LCD, SSFLCD, ect.

What is claimed is:

1. A liquid crystal display device comprising a pair of upper and lower substrates, transparent electrodes formed on said each substrate, orientation layers formed on said each transparent electrode and liquid crystal injected between said orientation layers, characterized in that said orientation layer comprises fluorine-containing poly-1,4-phenylenevinylene represented as the following formula (II),

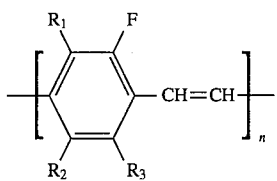

wherein $R_1$, $R_2$ and $R_3$ are independently $\bar{H}$ or F, and n is an integer of 100 or more.

2. A liquid crystal display device as claimed in claim 1, wherein said fluorine-containing poly-1,4-phenylenevinylene is formed by converting a sulfonium precursor polymer of fluorine-containing poly-1,4-phenylenevinylene by heat treatment during manufacture of said liquid crystal display device.

3. A liquid crystal display device as claimed in claim 1, wherein the pretilt angle of said liquid crystal is ranged from 5° to 20°.

* * * * *